United States Patent [19]

Spielvogel et al.

[11] Patent Number: 5,455,233
[45] Date of Patent: Oct. 3, 1995

[54] OLIGORIBONUCLEOSIDE AND OLIGODEOXYRIBONUCLEOSIDE BORANOPHOSPHATES

[75] Inventors: Bernard F. Spielvogel, Raleigh; Anup Sood, Durham; Iris H. Hall, Chapel Hill; Barbara R. Shaw, Durham, all of N.C.

[73] Assignees: University of North Carolina, Chapel Hill; Duke University, Durham; Boron Biologicals, Inc., Raleigh, all of N.C.

[21] Appl. No.: 953,820

[22] Filed: Sep. 30, 1992

Related U.S. Application Data

[62] Division of Ser. No. 443,781, Nov. 30, 1989, Pat. No. 5,177,198.

[51] Int. Cl.$^6$ .................... A61K 31/70; A61K 31/69; C07H 21/00; C07H 23/00
[52] U.S. Cl. ................ 514/44; 514/64; 536/23.1; 536/25.6
[58] Field of Search .................. 514/44, 64; 536/23.1, 536/17.1, 25.6

[56] References Cited

U.S. PATENT DOCUMENTS

| | | | |
|---|---|---|---|
| 4,672,110 | 6/1987 | Letsinger | 536/25.31 |
| 4,689,320 | 8/1987 | Kaji | 514/44 |
| 4,808,708 | 2/1989 | Yoshida et al. | 536/25.34 |
| 4,835,263 | 5/1989 | Nguyen et al. | 536/24.3 |
| 5,130,302 | 7/1992 | Spievogel et al. | 514/45 |

OTHER PUBLICATIONS

"Antisense Molecular Biology and S–oligos," *Synthesis* 1, No. 1, (pub. by Synthecell Corp., Rockville, Md.) (Oct. 1988).
"A Suitable Case for Irradiation," *Borax Review*, No. 3, 7 (1988).
Kabalka, et al., "Boron–11 MRI and MRS of Intact Animals Infused with a Boron Neutron Capture Agent," *Maganetic Resonance in Medicine* 8, 231 (1988).
Reetz, "Trialkyl Phosphite Borines. A New Type of Phosphorus–boron Compound," *J. Am. Chem. Soc.* 82, 5039 (1960).
Cover Sheet for the North Carolina Biotechnology Center Competitive Grants Program. Project Entitled "Boron Nucleic Acids," Jan. 1987.
Cover Sheet for the North Carolina Biotechnology Center Economic Development Grants Program. Project Entitled "Boronated Nucleosides," Apr. 1988.
The Source of Bioprocess/Biotechnology News, "Oligonucleotides Show Promise in Wide Range of Applications," vol. 9, No. 8, Sep. 1989.

*Primary Examiner*—Douglas W. Robinson
*Assistant Examiner*—James O. Wilson
*Attorney, Agent, or Firm*—Bell, Seltzer, Park & Gibson

[57] ABSTRACT

Disclosed are oligonucleoside boranophosphates, or salts thereof, comprising a chain of natural or modified ribonucleotides or deoxyribonucleotides, containing at least one boronated internucleotide phospodiester linkage of the formula:

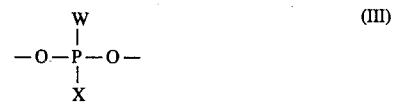

(III)

W is selected from the group consisting of =O, =S, —OPr, and —SPr where Pr is a base-labile protecting group. X is selected from the group consisting of —BH$_3$, —BH$_2$R$_1$, —BHR$_1$R$_2$ and —BR$_1$R$_2$R$_3$. R$_1$ is selected from the group consisting of —R$_4$, —COOH, —COOR$_4$, —CONHR$_4$, —CON(R$_4$)$_2$, —CN$^+$R$_4$Z$^-$, wherein Z$^-$ is an anion, —CN, carboxycholesteryl and carboxybenzyl, wherein R$_4$ is C1 to C18 alkyl. R$_2$ is selected from the group consisting of —R$_5$, —COOH, —COOR$_5$, —CONHR$_5$, —CON(R$_5$)$_2$, —CN$^+$R$_5$Z$^-$, wherein Z$^-$ is an anion, —CN, carboxy- cholesteryl and carboxybenzyl, wherein R$_5$ is C1 to C18 alkyl. R$_3$ is selected from the group consisting of C1 to C3 alkyl. Most preferably, X is —BH$_3$ and W is =0.

Compounds of Formula (III) are useful as antisense agents and probes in molecular biology, and have pharmacological activities including anti-inflammatory, antihyperlipidemic, and antineoplastic activity.

39 Claims, No Drawings

OLIGORIBONUCLEOSIDE AND OLIGODEOXYRIBONUCLEOSIDE BORANOPHOSPHATES

This application is a division of application Ser. No. 07/443,781, filed 30 Nov. 1989, now issued as U.S. Pat. No. 5,177,198.

FIELD OF THE INVENTION

The present invention relates to oligonucleotide derivatives having a boron-containing group substituted on an internucleotide phosphodiester linkage.

BACKGROUND OF THE INVENTION

Synthetic oligonucleotides are currently attracting considerable attention as probes for molecular biology and as potential therapeutic agents. See C. Marcus-Sekura, 172 *Anal. Biochem.* 289 (1988); F. Eckstein, 22 *Angew Chem., Int. Ed.* 423 (1983); F. Eckstein, 54 *Ann Rev. Biochem.* 367 (1985); M. Hamblin et al., 241 *Biochem. J.* 827 (1987); R. Letsinger et al., 110 *J. Am. Chem. Soc.* 4470 (1988); P. Miller et al., in *Nucleic Acids; The Vectors of Life*, 521 (B. Pullman and J. Jortner Eds., 1983); P. Miller and P. Ts'so, 2 *Anticancer Drug Design* 117 (1987); P. Sarin et al., 85 *Proc. Natl. Acad. Sci. U.S.A.* 7488 (1988); M. Matsukura et al., 86 *Proc. Natl. Acad. Sci. U.S.A.* 4244 (1989); C. Smith et al., 83 *Proc. Natl. Acad. Sci. U.S.A.* 2787 (1985); S. Agrawal et al., 85 *Proc. Natl. Sci. U.S.A.* 7079 (1988). Thus, oligonucleotides with modified backbones, also known as "antisense" agents, may be used to inhibit or control growth of viruses as well as to specifically control the expression of genes concerned with genetic disorders.

The naturally occuring oligonucleotides and oligodeoxynucleotides contain an internucleotide phosphodiester linkage of the formula:

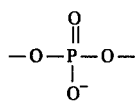
(I)

Several modifications of the internucleotide phosphodiester linkage have been made. Exemplary is the methylphosphonate, which has the formula:

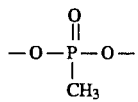
(II)

See P. Miller et al., 18 *Biochemistry* 5134 (1979). Other modifications which have been made include the phosphotriester (—P—OR), See P. Miller et al., 93 *J. Am. Chem. Soc.* 6657 (1971); the phosphorothioate (—P—S), See P. Burgers and F. Eckstein, 18 *Biochemistry* 592 (1979), the phosphorodithioate (S—P—S), See W. Brill et al. 111 *J. Am. Chem. Soc.* 2321 (1989), and the phosphoramidate (—P—NR$_2$), See K. Ogilvie and J. Nemer, 21 *Tetrahedron Lett.* 4145 (1988). Such modified oligonucleotides have been shown to inhibit viruses such as HIV, HSV, etc., and the expression of oncogenes such as c-myc and c-Ha-ras. See C. Stein and J. Cohen, 48 *Cancer Res.* 2659 (1988); C. Markus-Sekura et al. 15 *Nucl. Acids Res.* 5749 (1987); R. Meikkila et al., 328 *Nature* 445 (1987).

While it is clear that considerable potential exists for modified oligonucleotides as both probes and potential therapeutic agents, it is equally clear that a considerable effort is required to translate this field into new and useful compounds. The present invention arose from our ongoing research into new oligonucleotides useful as gene probes and as potential therapeutic agents.

SUMMARY OF THE INVENTION

We herein disclose the first examples of oligonucleotides with a boronated internucleotide phosphodiester linkage, thus establishing an entirely new class of nucleic acid derivatives. More particularly, disclosed herein is an oligoribonucleoside or oligodeoxyribonucleoside boranophosphate, or a salt thereof, comprising a chain of natural or modified nucleotides or deoxynucleotides containing at least one boronated internucleotide phospodiester linkage of the formula:

(III)

wherein:

W is selected from the group consisting of =O, =S, —OPr, and —SPr where Pr is a base-labile protecting group (i.e., leaving group) which can be removed from the oxygen or sulfur by a strong base to yield =O or =S as W during the synthesis of the oligonucleotide by the phosphite-triester method. Preferably, W is selected from the group consisting of =O, =S, =OR', =SR', and —OCH$_2$CH$_2$CN, wherein R' is C1 to C3 alkyl, preferably methyl. Compounds in this group having —OR', —SR', or —OCH$_2$CH$_2$CN as W are useful as intermediates for making compounds having as W =O or =S, and compounds in this group having =O, =S, —OR' and —SR' are useful as products in the methods of use discussed below. Compounds having =O as W are the most preferred products, and compounds having —OCH$_3$ as W are the most preferred intermediates.

X is selected from the group consisting of —BH$_3$, —BH$_2$R$_1$, —BHR$_1$R$_2$ and —BR$_1$R$_2$R$_3$. Preferably, X is —BH$_3$, —BH$_2$R$_1$, or —BHR$_1$R$_2$. More preferably, X is —BH$_3$ or —BH$_2$R$_1$. Most preferably, X is —BH$_3$.

R$_1$ is selected from the group consisting of —R$_4$, —COOH, —COOR$_4$, —CONHR$_4$, —CON(R$_4$)$_2$, —CN$^+$R$_4$, —CN, carboxycholesteryl and carboxybenzyl, wherein R$_4$ is C1 to C18 alkyl. Preferably R$_1$ is —R$_4$, —COOH, —COOR$_4$, —CONHR$_4$, —CON (R$_4$)$_2$, —CN$^+$R$_4$, or —CN; more preferably R$_1$ is —R$_4$, —COOH, —COOR$_4$, —CONHR$_4$, —CON (R$_4$)$_2$, or —CN; most preferably R$_1$ is —R$_4$ or —CN. Preferably R$_4$ is C1 to C9 alkyl and more preferably R$_4$ is C1 to C3 alkyl.

R$_2$ is selected from the group consisting of —R$_5$, —COOH, —COOR$_5$, —CONHR$_5$, —CON (R$_5$)$_2$, —CN$^+$R$_5$, —CN, carboxycholesteryl and carboxybenzyl, wherein R$_5$ is C1 to C18 alkyl. Preferably R$_2$ is —R$_5$, —COOH, —COOR$_5$, —CONHR$_5$, —CON (R$_5$)$_2$, —CN$^+$R$_5$, or —CN; more preferably R$_2$ is —R$_5$, —COOH, —COOR$_5$, —CONHR$_5$, —CON (R$_5$)$_2$, or —CN;, still more preferably R$_2$ is —R$_5$ or —COOH, and most preferably R$_2$ is —R$_5$. Preferably R$_5$ is C1 to C9 alkyl; more preferably R$_5$ is C1 to C3 alkyl; and most preferably R$_5$ is methyl.

R$_3$ is selected from the group consisting of C1 to C3 alkyl, preferably methyl.

Oligonucleotides and oligodeoxynucleotides containing a boronated internucleotide phosphodiester linkage represent an important, and perhaps ideal, species in that the nucleotide bases are unaltered (thus maintaining binding specificity) and the backbone may remain negatively charged (for water solubility) like the natural O-oligos of Formula (I). Since $BH_3$ is much more hydrophobic than oxygen, it should impart a greater membrane permeability than the O-oligo and yet maintain nuclease resistance like the methylphosphonates illustrated in formula (III). Although compounds containing boron-hydride bonds are susceptible to hydrolysis, the B—H bond in boranophosphates possesses unusual hydrolytic stability. Moreover, since these nucleic acids contain boron, the additional advantage of using the unique neutron capturing ability of the non-radioactive $^{10}B$ isotope, R. G. Fairchild and G. L. Brownell, Editors "Proceedings of the First International Symposium on Neutron Capture Therapy", Oct. 12–14, 1983, as a label in a probe or as a therapeutic agent also exists. For this purpose, boron used to make the compounds of the present invention may be $^{10}B$ enriched.

DETAILED DESCRIPTION OF THE INVENTION

Oligonucleotides of the present invention may, apart from the inventive boron-containing linkage, be polymers of the naturally occuring nucleotides, modified nucleotides, or of both naturally occuring and modified nucleotides. Modifications may be to the internucleotide phosphodiester linkages, to the nucleosides, or to both.

Thus, the nucleoside base may be a natural base, such as adenine, thymine, cytosine, guanine, uracil, xanthine, or hypoxanthine, (the latter two being the natural degradation products) or in derivatives may be the base of a modified nucleic acid such as 4-acetylcytidine; 5-(carboxyhydroxylmethyl)uridine; 2'O-methylcytidine; 5-carboxymethylaminomethyl-2-thiouridine; 5-carboxymethylaminomethyluridine; dihydrouridine; 2'O-methylpseudouridine; beta,D-galactosylqueosine; 2'O-methylguanosine; N6-isopentenyladenosine; 1-methyladenosine; 1-methylpseudouridine; 1-methylguanosine; 1-methylinosine; 2,2-dimethylguanosine; 2-methyladenosine; 2-methylguanosine; 3-methylcytidine; 5-methylcytidine; N6-methyladenosine; 7-methylguanosine; 5-methylaminomethyluridine; 5-methoxyaminomethyl-2-thiouridine; beta,D-mannosylqueosine; 5-methoxycarbonylmethyluridine; 5-methoxyuridine; 2-methylthio-N6-isopentenyladenosine; N-((9-beta-D-ribofuranosyl-2-methylthiopurine-6-yl)carbamoyl)threonine; N-((9-beta-D-ribofuranosylpurine-6-yl)N-methyl-carbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'O-methyl-5-methyluridine; and 2'O-methyluridine.

Derivatives may be formed by modifying the internucleotide phosphodiester linkage. Internucleotide phosphodiester linkages in the chain may be modified, for example, to the methylphosphonate, the phosphotriester, the phosphorothioate, the phosphorodithioate, and the phosphoramidate (see Formula II above and accompanying text).

Derivatives may be formed by modifying the 3' or 5' end of the oligonucleotide. Groups which can be added to the 3' or 5' end vary widely, from relatively inert protecting groups to reactive groups or groups with special properties to obtain desireable physical, chemical, or biochemical effects. For example, derivatives may be formed by joining an intercalating agent to the oligonucleotide in the manner described in U.S. Pat. No. 4,835,263 to Nguyen et al. (the disclosure of this and all other patent references cited herein is to be incorporated herein by reference). A wide variety of protecting groups can be substituted on the 5' and 3' hydroxy groups (e.g., of compounds of Formula (IV) below), such as the triphenylmethyl (trityl) group and its derivatives on the 5' hydroxy group, and acetyl, benzoyl, or the 3'O-succinyl group on the 3' hydroxy group, as known in the art. See, e.g., 1 Chemistry of Nucleosides and Nucleotides, 287–92 (L. Townsend ed. 1988). In general, the 5' hydroxy group is protected with an acid labile group and the 3' hydroxy group is protected with an acyl group. Id. at 289 (When the 5' hydroxyl group is protected with an acid labile group such as mono- and dimethoxytrityl, the 3'-hydroxyl group of deoxynucleosides can be protected with acyl groups.).

A preferred group of oligonucleoside boranophosphates, or salts thereof, of Formula (III) above have the formula, from 5' to 3' of Formula (IV):

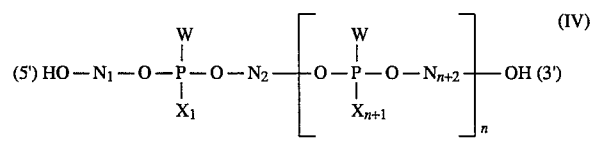

In Formula (IV) The value of n is not critical. Typically, n is an integer having a value of from 0 to 50, depending upon the number and placement of boron-containing groups and the particular synthetic scheme employed. When n is 0 the bracketed group is absent and $N_2$ is bound to the 3'—OH group, as shown. Preferably, n has a value of from 0 to 30, more preferably n has a value of from 0 to 18, and most preferably, n has a value of from 0 to 3.

W in Formula (IV) is as given in connection with formula (III) above.

$X_1$ through $X_{n+1}$ in Formula (IV) are each independently selected from the group consisting of —OH, —$BH_3$, —$BH_2R_1$, —$BHR_1R_2$ and —$BR_1R_2R_3$, subject to the proviso that at least one of $X_1$ through $X_{n+1}$ is not —OH. The —OH group may, of course, exist as —O$^-$ in salts of the compounds of formula (IV). Preferably, at least $X_1$ and $X_{n+1}$ are not —OH. Most preferably, $X_1$ through $X_{n+1}$ are not —OH.

$R_1$, $R_2$, and $R_3$ in Formula (IV) are as given in connection with formula (III) above.

$N_1$ through $N_{n+2}$ are each independently a nucleoside or deoxynucleoside monomer of the formula:

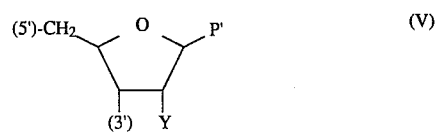

Y is selected from the group consisting of —H (the deoxyribonucleoside) and —OH (the ribonucleoside). Preferably Y is —H.

P' is a base of a natural or modified nucleic acid, which are discussed in detail above above. Preferably, P' is selected from the group consisting of adenine, thymine, cytosine, guanine, uracil, xanthine, hypoxanthine, 5-methylcytosine, 5-bromouracil, 8-azidoadenine, and 2,6-diaminopurine. Most preferably, P' is adenine, thymine, cytosine, guanine, or uracil.

In nucleosides and deoxynucleosides, the pentose is joined to the base by a β-N-glycosyl bond between carbon atom 1 of the pentose and either nitrogen atom 9 of purine bases (and their derivatives) or nitrogen atom 1 of pyrimidine bases (and their derivatives). The phosphate group of a nucleotide is in ester linkage with carbon atom 5 of the pentose. In a polynucleotide chain, the phosphate group of a nucleotide is additionally in ester linkage with carbon atom 3 of the pentose in the adjacent nucleotide to form the phosphodiester internucleotide bond.

The term "alkyl," as used herein, refers to linear or branched alkyl groups which may be saturated or unsaturated. Preferred alkyl groups in the compounds of Formula (III) are linear and saturated.

The following compounds are exemplary of the compounds of Formula (III):

(A) thymidylyl[3'-5']-(3'-acetylthymidylyl) (borane)phosphonate methyl ester (or 3'-0[thymidylyl]-5'-0[3'-acetylthymidylyl]methyl phosphite-borane);

(B) thymidylyl[3'-5']-(3'-acetylthymidylyl) (cyanoborane)phosphonate methyl ester;

(C) thymidylyl[3'-5']-(3'-acetylthymidylyl) (carbomethoxyborane)phosphonate methyl ester;

(D) thymidylyl[3'-5']-(3'-acetylthymidylyl) (N-ethylcarbamoylborane)phosphonate methyl ester;

(E) thymidylyl[3'-5']-(3'-acetylthymidylyl) (carboxyborane)phosphonate methyl ester;

(F) thymidylyl[3'-5']-(3'-acetylthymidylyl) (N-ethylcarbamoyl)methylborane phosphonate methyl ester;

(G) 2'deoxyadenylyl[3'-5']-(3'acetyl-2'deoxyadenylyl)boranephosphonate methyl ester;

(H) 2'deoxyguanylyl[3'-5']-(3'acetyl-2'deoxyguanylyl)boranephosphonate methyl ester;

(I) 2'deoxyguanylyl[3'-5']-(3'-acetyl-2'deoxyguanylyl) (cyanoborane) phosphonate methyl ester;

(J) thymidylyl[3'-5']-thymidylyl(borane)phosphonate, ammonium salt;

(K) thymidylyl[3'-5']-thymidylyl(cyanoborane)phosphonate, ammonium salt;

(L) thymidylyl[3'-5']-thymidylyl(carbomethoxy)phosphonate, ammonium salt;

(M) thymidylyl[3'-5']-thymidylyl(methylborane)phosphonate, ammonium salt;

(N) thymidylyl[3'-5']-thymidylyl(N-ethylcarbamoyl)methylborane phosphonate, ammonium salt;

(O) 2'deoxycytidylyl[3'-5']-2'deoxycytidylyl(borane)phosphonate ammonium salt;

(P) 2'deoxycytidylyl[3'-5']-2'deoxycytidylyl(cyanoborane)phosphonate ammonium salt;

(Q) 2'deoxyadenylyl[3'-5']-2'deoxyadenylyl(cyanoborane)phosphonate ammonium salt;

(R) thymidylyl[3'-5']2'-deoxyadenylyl[3'-5']-2'-deoxyguanylyl(borane)phosphonate dimethyl ester;

(S) thymidylyl[3'-5']2'-deoxyadenylyl[3'-5']-2'-deoxyguanylyl(cyanoborane)phosphonate dimethyl ester;

(T) thymidylyl[3'-5']thymidylyl[3'-5'](3'-acetylthymidylyl) boranephosphonate dimethyl ester;

(U) thymidylyl[3'-5']thymidylylboranephosphonate[3'-5'] (3'-acetylthymidylyl) cyanoboranephosphonate dimethyl ester;

(V) tetra(thymidine boranephosphonate); and (W) hexa(adenine boranephosphonate).

Compounds of the present invention are preferably made by the reactions shown in Scheme 1 below.

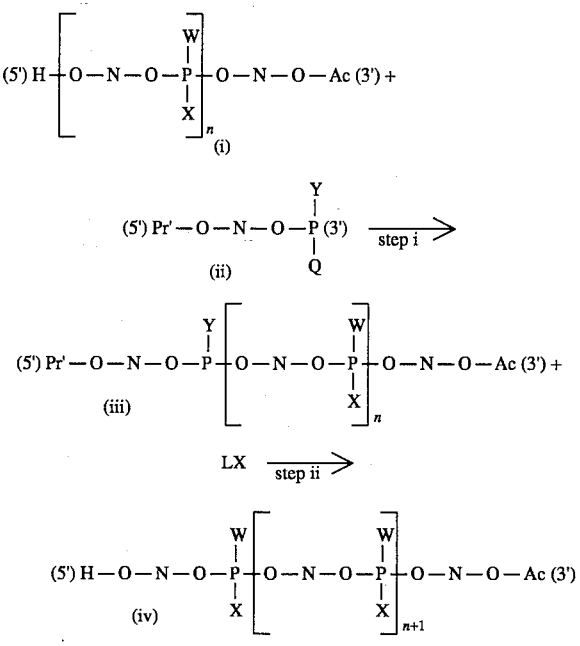

Scheme 1

As shown in Scheme 1, boronated oligonucleotides of the present invention are prepared by a modification of the phosphite-triester method, see generally 1 Chemistry of Nucleosides and Nucleotides, 310–19 (L. Townsend Ed. 1988), in which the step of oxidizing the phosphite linkage of the intermediate (step ii) to form a phosphate linkage is carried out with an adduct of a Lewis base and a boron-containing group (LX). Ordinarily, the phosphite-triester method involves a chain elongation condensation reaction, an oxidation reaction to convert the intermediate phosphite to the phosphate, and a 5' deprotection step so that the chain elongation reaction may be repeated and the cycle of steps continued. When the reaction described herein is carried out with excess adduct, the 5' deprotection step may be advantageously eliminated.

As shown in scheme 1, compound (i) is condensed with compound (ii) in step i to give compound (iii); compound (iii) is oxidized with LX in step ii to give compound (iv). To continue the chain elongation cycle, step i is repeated with compound (iv) taking the place of compound (i), and step ii then optionally repeated. This cycle of steps is repeated until a chain of the desired length, as discussed in connection with Formula (iv) above, is reached. In the first cycle, n is zero.

Pr' represents any 5' protecting group, as discussed above, but is preferably Lewis acid labile. Ac represents an acyl group (for liquid phase synthesis) or a solid support (for solid phase synthesis), as also discussed above. Y represents Pr-V, where Pr is a protecting group and V is S or O (V being covalently bound to P), as given in connection with Formula III above. Q is a proton accepting group which is a stronger proton acceptor than the 5' oxygen in compound (i). Any protecting group and proton accepting group may be employed which is employed in the phosphite-triester method, with Pr and Q determined by the particular phosphitylating reagent employed. Phosphitylating reagents have the general formula Y-P. See Chemistry of Nucleosides and Nucleotides, 310–14 (L. Townsend Ed. 1988). The phosphitylating reagent is not shown in Scheme 2, but may be any phosphitylating reagent which may be reacted with a 5'-protected nucleoside to prepare compound (ii). Thus, Pr may for example be C1 to C3 alkyl, 2,2,2-tribromoethyl-, benzyl-, 2-cyanoethyl-, 2-methylsulfonylethyl, 4-nitrophenylethyl, 2-chlorophenyl, p-chlorophenyl-, phenylethyl- or p-nitrophenylethyl-, and Q may for example be chlorine, 1-substituted 1,2,4-triazole, or 1-substituted 1,2,3,4-tetrazole. See Id.

A particularly preferred method of preparing compounds of the present invention is given in Scheme 2 below.

In step (i) of Scheme 2, a 5'-DMT-nucleoside phosphoramidite is reacted with a 3'-acylnucleoside in the presence of tetrazole to form an intermediate phosphite, which phosphite is converted in step (ii) to a 3'-acyloligonucleotide (1) having an internucleotide phosphodiester linkage as given in Formula (III) above by oxidation with LX, where L is a Lewis base, such as —S(CH$_3$)$_2$ or —N(CH$_3$)$_3$, which is a weaker electron donors than the internucleotide phosphorus Scheme 2

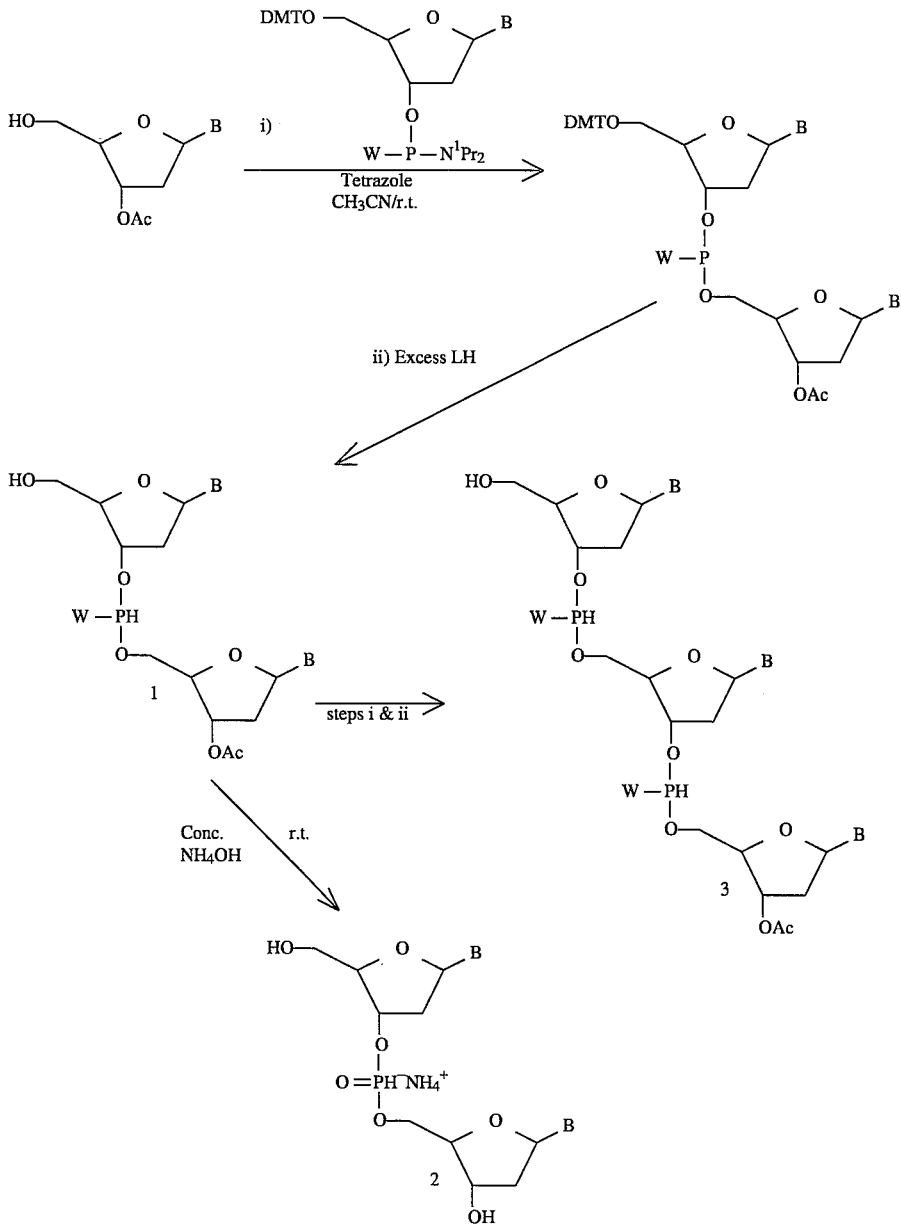

In scheme 2, the substituents W and X are as given above. DMT refers to a dimethoxytrityl protecting group, but may be any suitable 5' protecting group as discussed above. Ac is an acyl group such as acetyl (Ac represents a solid support in solid-phase synthesis, as discussed in greater detail below). The substituent B on the ribose refers to the base purine, pyrimidine, or derivative thereof, as identified by substituent P' in connection with Formula (V) above.

(The strong Lewis base properties of Trialkylphosphites are described in T. Reetz, Trialkyl Phosphite Borines. A New Type of Phosphorus-boron Compound, *J. Am. Chem. Soc.* 82, 5039 (1960)). For chain elongation, steps (i) and (ii) are then repeated, with the product of step (ii) being reacted with a 5'-DMT-nucleoside, to form oligonucleotides of greater length (e.g., the trimer 3). Alternatively, the 3'-acyloligonucleotide (1) may be hydrolyzed with a strong base to remove the 3' acyl group and restore the 3' hydroxyl group as in compound (2), and remove the protecting group Pr in X.

Solid phase synthesis for the above-described scheme is implemented by esterifying the 3' carbon of the substrate nucleotide to an insoluble support instead of an acyl group (as is done for liquid phase synthesis). Solid phase synthesis for the phosphite-triester method is known, and the insoluble support may be any of those conventionally employed, such as controlled pore glass. See generally 1 Chemistry of Nucleosides and Nucleotides, 314–19 (L. Townsend ed. 1988).

Side reactions with bases, e.g., when the base is Adenine or Cytosine (hydroboration of the carbon-carbon double bond) may be eliminated by replacing $Me_2SX$ in the substitution step with $Me_3NX$ since $Me_3NX$ is a much weaker hydroboration agent than $Me_2SX$. While phosphites easily displace trimethylamine from $Me_3NX$, weakly basic nucleoside bases will not react with this compound. Other borane sources, such as $Ph_3PX$ or aniline borane may also give satisfactory results.

When the boronating agent is a substituted borane, such as $Me_2SBH_2CN$, since the $BH_2CN$ species is a less powerful hydroborating agent, hydroborated side products with the C—C double bond with Adenine or Cytosine should be greatly lessened.

Since the phosphorus donor base in $(RO)_3P$ is stronger than amine, ethers, sulfides, etc. (T. Reetz, *J. Amer. Chem. Soc.* 82, 5039 (1960)) even if initial formation of a purine or pyrimidine nitrogen base.X adduct takes place, the thermodynamically more stable phosphorus.X will eventually be formed. Additionally, since the P.X species are expected to possess high hydrolytic stability, any purine or pyrimidine nitrogen base.X adduct may be removed by appropriate hydrolysis with acid or base.

The reaction of an intermediate dinucleotide phosphite with $Ph_3PBH_2CN$ or $PhNH_2BH_2CN$ has been carried out at room temperature and 68° C. without success. It appears that the $Ph_3P$ or $NH_2Ph$ are more difficult to displace than $Me_2S$. Thus, by using a weaker Lewis base ($Me_2S$) adduct of $BH_2CN$, i.e., $Me_2SBH_2CN$ or $(BH_2CN)_x$ itself, formation of the phosphorus-$BH_2CN$ should readily take place.

Compounds of Formula (III) which are capable of binding to polydeoxyribonucleic acid or polyribonucleic acid are useful as probes in molecular biology. These probes can be used in any suitable environment, such as Southern blotting and Northern blotting, the details of which are known. See, e.g., R. Old and S. Primrose, Principles of Gene Manipulation, 8–10 (3d Ed. 1985). When used as probes, the boron atom serves essentially as a radiolabel, though it is not itself radioactive until exposed to thermal neutron radiation (low energy neutrons). When exposed to low energy neutrons, $^{10}B$ absorbs a neutron and forms $^{11}B$, which rapidly decays and releases an alpha particle, thus providing a detectable signal. The techniques involved in the generation of the alpha particle are known. See, e.g., A. Soloway, *Borax Rev.* 3, 7–9 (1988).

Probes of the present invention can be used by contacting the probe (which is capable of selectively binding to a predetermined polydeoxyribonucleic acid or polyribonucleic acid sequence) to a substrate DNA or RNA sample suspected of containing the predetermined sequence so that the compound of Formula (III) will bind to the predetermined sequence if the predetermined sequence is present. The requirements for selective binding are known, as is the case with antisense agents. Next, unbound probe is removed from the substrate, and the substrate is exposed to thermal radiation. The release of alpha particles from the substrate indicates that the predetermined sequence is present in the substrate. The procedure may be carried out on single-stranded substrate DNA which is immobilized on a nitrocellulose support, which support is then placed in a solution containing the probe, then washed, then placed in contact with photographic film and exposed to thermal radiation, as in a Southern blot. The procedure may be carried out in like manner with an RNA substrate covalently bound to reactive paper (e.g., paper prepared by diazotization of aminobenzyloxymethyl-paper), as in a Northern blot. Conventional techniques for neutron capture radiography may be employed. See D. Gabel et al., *Cancer Res.* 47, 5451 (1987).

Boron probes may be detected in vivo by $^{11}B$ multinuclear magnetic resonance imaging (MRI) and spectroscopy, see, e,g,, G. Kabalka et al., *Magnetic Resonance in Medicine* 8, 231 (1988), by administering the probe to an animal subject and detecting the probe by $^{11}B$ MRI, in accordance with known procedures.

The compounds of the present invention have pharmaceutical activity, including anti-inflammatory, and antihyperlipidemic activity.

A method of combatting hyperlipidemia in an animal subject comprises administering an animal subject in need of such treatment a hyperlipidemia-combatting amount of a compound of Formula (III).

A method of producing an anti-inflammatory response in an animal subject in need of such treatment comprises administering an animal subject an inflammation-combatting amount of a compound of Formula (III).

Subjects to be treated by the methods of the present invention include both human and animal (e.g., bird, dog, cat, cow, horse) subjects, and are preferably mammalian subjects.

Animal subjects are administered compounds of Formula (III) at a daily dose of preferably at least about 0.1 mg/kg, more preferably at least about 0.5 mg/kg, and most preferably at least about 2 mg/kg. The daily dose is preferably not more than about 1000 mg/kg, more preferably not more than about 200 mg/kg, and most preferably not more than about 50 mg/kg.

As noted above, the compounds of Formula (III) may be administered per se or in the form of a pharmaceutically acceptable salt. When used in medicine, the salts of the compound of Formula (III) should be both pharmacologically and pharmaceutically acceptable, but non-pharmaceutically acceptable salts may conveniently be used to prepare the free active compound or pharmaceutically acceptable salts thereof and are not excluded from the scope of this invention. Where appropriate, such pharmacologically and pharmaceutically acceptable salts include, but are not limited to, those prepared from the following acids: hydrochloric, hydrobromic, sulphuric, nitric, phosphoric, maleic, acetic, salicylic, p-toluenesulfonic, tartaric, citric, methanesulphonic, formic, malonic, succinic, naphthalene-2-sulphonic and benzenesulphonic. Also, where appropriate, pharmaceutically acceptable salts can be prepared as alkaline metal or alkaline earth salts, such as the sodium, potassium or calcium salts of a carboxylic acid group.

The present invention also provides pharmaceutical formulations, both for veterinary and for human medical use, which comprise the active agent (the compound of Formula (III)) together with one or more pharmaceutically acceptable carriers thereof and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, in a quantity appropriate to achieve the desired daily dose.

The formulations include those suitable for oral, rectal, topical, nasal, ophthalmic or parenteral (including subcutaneous, intramuscular and intravenous) administration. Formulations suitable for parenteral administration are preferred.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into desired formulations.

Formulations of the present invention suitable for oral administration may be presented as discrete units such as capsules, cachets, tablets or lozenges, each containing a predetermined amount of the active ingredient as a powder or granules; or a suspension in an aqueous liquor or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with a suitable carrier may be made by molding in a suitable machine.

A syrup may be made by adding the active compound to a concentrated aqueous solution of a sugar, for example sucrose to which may also be added any accessory ingredient(s). Such accessory ingredient(s) may include flavorings, suitable preservatives, an agent to retard crystallization of the sugar, and an agent to increase the solubility of any other ingredient, such as a polyhydric alcohol, for example glycerol or sorbitol.

Formulations suitable for parenteral administration conveniently comprise a sterile aqueous preparation of the active compound, which is preferably isotonic with the blood of the recipient (e.g., physiological saline solution).

Nasal spray formulations comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical pharmaceutical formulations.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

The following Examples are provided to illustrate the present invention, and should not be construed as limiting thereof. Compounds referenced by numbers refer to the compounds illustrated in the schemes above, and compounds referenced by letters refer to the compounds named in the alphabetic list above.

EXAMPLE 1

Synthesis of Thymidylyl[3'-5'](3'-acetylthymidylyl) borane-phosphonate methyl ester (Compound A)

Boronated oligonucleotides were prepared according to the method described in Scheme 2. Tetrazole (0.50 g, 7.14 mmol, 5 equiv.) was dissolved in freshly dried $CH_3CN$ (15 ml, dried by refluxing over $CaH_2$, followed by distillation under Argon) under argon. To this 5'-O-DMT-thymidine-3'-(Methyl-N,N-diisopropyl) phosphoramidite (1.00 g, 1.42 mmol) dissolved in 10 ml dry $CH_3CN$ was added by a syringe. The phosphoramidite sample vial was rinsed with another 3–4 ml of dry $CH_3CN$ and this was also transferred by a syringe to the reaction flask. To this mixture 3'-O-acetylthymidine (0.404 g, 1.42 mmol) was added and the mixture was stirred at room temperature. After 15 minutes and complete disappearance of white solid, $Me_2S.BH_3$ (0.468 ml of 10M solution in $Me_2S$, 3.3 equiv.) was added. After complete disappearance of phosphite peaks in the $^{31}P$ nmr spectrum and appearance of peak due to the product, solvent was removed from the reaction mixture at room temperature under reduced pressure. The crude product was purified by flash chromatography on silica gel using EtOAc:Acetone (8.5:1.5). Further purification was achieved by reverse phase HPLC on a C-18 column (1 inch×25 cm) using a gradient system (25–100% B in 38 min., flow rate 9.2 ml/min). The solvents used for HPLC were water (Solvent A) and acetonitrile (Solvent B). Elemental analysis was: %H calc. 5.75, found 5.94; %C calc. 46.02, found 46.01; %N calc. 9.33, found 9.02; %P calc. 5.16, found 4.97.

EXAMPLE 2

Synthesis of Thymidylyl[3'-5']thymidylyl borane-phosphonate (Compound J)

Thymidylyl[3'-5'](3'-acetylthymidylyl)boranephosphonate methyl ester (40.7 mg, 0.068 mmol) was taken in conc. $NH_4OH$ (10 ml) in a sealed tube and was kept on a shaker at room temperature overnight. The tube was cooled and opened. The $NH_3$ was allowed to escape at room temperature. The solution was cooled to −80° C. and lyophilized to give 42 mg of crude product. The product was purified by reverse phase HPLC.

EXAMPLE 3

Synthesis of Thymidylyl[3'-5']thymidylyl 3',5'](3'-acetylthymidylyl)boranephosphonate dimethyl ester (Compound T)

To a solution of tetrazole (0.368 g, 5.25 mmol, 5 equiv.) in dry $CH_3CN$ (15 ml) was added a solution of 5'-DMT-thymidine-5'-(methyl-N,N-diisopropyl) phosphoramidite (0.750 g, 1.063 mmol). To this mixture, Thymidylyl[3'-5'](3'-acetylthymidylyl)boranephosphate methyl ester (0.630 g, 1.049 mmol) was added and the mixture was stirred at room temperature for 40 minutes. To this $Me_2S.BH_3$ (346 µl of 10M solution in $Me_2S$, 3.3 equiv.) was added and the mixture was stirred at room temperature for 4 hours. The solvent was removed and the crude product was purified by flash chromatography on silica gel using EtOAc:Acetone (8:2). Further purification was achieved by reverse phase HPLC using a gradient of 25–52.5% B in 20 min at a flow rate of 9.2 ml/min. Solvents used were water (Solvent A) and $CH_3CN$ (Solvent B).

EXAMPLE 4

Synthesis of (C⁶N-Benzoyladenylyl)-[3'-5']-(3'-acetylthymidylyl)boranephosphonate methyl ester Tetrazole (0.430 g, 6.138 mmol) was dissolved in dry $CH_3CN$ (13 ml) under Argon. To this C⁶N-Benzoyl-5'-O-DMT-adenine-3'(methyl-N,N-diisopropyl)phosphoramidite (1.00 g, 1.22 mmol) dissolved in $CH_3CN$ (10 ml) was added by a syringe. The phosphoramidite vial was rinsed with 3–4 ml of $CH_3CN$ which was added to the reaction mixture. To this 3'-0-acetylthymidine (0.347 g, 1.22 mmol) was added and the mixture was stirred at room temperature for 40 minutes. $Me_2S.BH_3$ (403 ml of 10M solution in $Me_2S$, 3.3 equiv.) was added to the reaction mixture and after ten minutes a small portion was taken in $CDCl_3$ for $^{31}P$ nmr. NMR showed formation of desired boranephosphonate, as well as small amount of unreacted intermediate phosphite. So another 100 µl of $Me_2BH_3$ was added and the mixture was stirred for thirty minutes. The solvent was removed under reduced pressure and the product was partially purified by flash chromatography on silica gel using EtOAc:Acetone (8.5:1.5).

EXAMPLE 5

Synthesis of (C⁴N-benzoylcytidylyl)-[3'-5']-(3'-acetylthymidylyl)boranephosphonate methyl ester To a solution of tetrazole (0.397 g, 5.667 mmol), 5 equiv.) in freshly dried $CH_3CN$ (15 ml) under argon, was added a solution of phosphoramidite (0.900 g, 1.132 mmol) in dry $CH_3CN$ (5 ml). The phosphoramidite vial was rinsed with another 5 ml of $CH_3CN$ and the solution was transferred to the reaction flask. To this mixture was added 3'-acetylthymidine (0.322 g, 1.133 mmol) and the mixture was stirred at room temperature for 40 minutes. To this, $Me_2S.BH_3$ (374 ml of 10M solution in $Me_2S$, 3.3 equiv.) was added and after 4.5 hours, $^{31}P$ nmr showed complete disappearance of intermediate phosphite and presence of desired product. The solvent was removed from the reaction mixture at room temperature under reduced pressure. The product was partially purified by flash chromatography on silica gel using EtOAc:Acetone (6:4).

EXAMPLE 6

Purification of Boronated Oligonucleotides with Bases Other Than Thymidine

Boron-containing dinucleotides where one of the bases is either A or C while the other is T have been synthesized (see Examples 4 and 5 above). In two cases, the reaction appears to be more complicated than when it was performed with just T as bases. Although the $^{31}P$ nmr shows a broad peak in the range of 116–117 ppm with very little oxidized phosphate and phosphoramidate species, tlc analysis shows a complex mixture. Both A-T and C-T dimers have been partially purified by flash chromatography.

One of the reasons for the complex mixture observed by tlc may have been the formation of amine-borane adducts of the bases. Since the reaction between $Me_2SBH_3$ and amines or phosphites is instantaneous and there are several places on A or C where an adduct or combination of adducts can form, the large number of products observed is not unusual. Amine boranes, however, are hydrolytically less stable than phosphite borane; therefore hydrolysis with mild acid could simplify the complex mixture. This reaction has been carried out in case of the A.T dimer and the tlc was thereby simplified.

Reaction of $Me_2SBH_3$ with 3',5'-silylated-deoxyguanosine as a model for reaction with G as one of the bases results in base-borane adduct formation. The product, however, slowly dissociates in solution to the starting nucleoside. Therefore, reaction of G containing dinucleotide phosphite with $Me_2SBH_3$ will probably result in adduct formation at both phosphorus and one of the base nitrogens (most likely N7). But slow dissociation of base-borane adduct in solution and stability of phosphite-borane adduct will ultimately lead to pure phosphite-borane if an equivalent amount of $Me_2SBH_3$ is used.

EXAMPLE 7

Antihyperlipidemic Activity

Compounds to be tested were suspended in 1% aqueous carboxymethylcellulose, homogenized and administered to male $CF_1$ mice (25 g) intraperitoneally for 16d. On days 9 and 16, blood was obtained by tail vein bleeding, and the serum was separated by centrifugation for three minutes. The serum cholesterol levels were determined by a modification of the Liebermann-Burchard reaction in accordance with known techniques. See A. Ness, et al., *Clin. Chim. Acta* 10, 229 (1964). Serum triglyceride levels were determined with a commercial kit, the Fisher Hycel Triglyceride Test Kit, for a different group of animals bled on day 16. The results of these antihyperlipidemic screens, for a compound dose of 8 mg/kg, are shown in Table 1 below.

TABLE 1

| | Percent Inhibition | | |
| --- | --- | --- | --- |
| | Serum Cholesterol | | Serum Triglyceride |
| Compound | Day 9 | Day 16 | Day 16 |
| (A) | 38 | 46 | 12 |
| (J) | — | — | — |
| (T) | 33 | 32 | 18 |

EXAMPLE 8

Anti-Inflammatory Activity $CF_1$ male mice (~25 g) were administered test drugs at 5–40 mg/kg in 0.05% Tween 80-$H_2O$ intraperitoneally 3 hours prior to and 30 minutes prior to the injection of 0.2 ml of 1% carrageenan in 0.9% saline into the plantar surface of the right hind foot. Saline was injected into the left hind foot, which serves as a base line. After 3 hours, both feet were excised at the tibiotarsal (ankle) joint according to standard procedures. See C. Winter et al., *Proc. Soc. Expt. Biol Med.* 544, 111 (1962); A. Roszkawski et al., *J. Pharm. Exp. Ther.* 179, 114 (1971). Control mice afforded a 78±3 mg increase in paw weight. Data on the percent inhibition of the inflammatory response for a dose of 8 mg/kg are reported in Table 2 below.

TABLE 2

| Compound | Percent Inhibition |
| --- | --- |
| (A) | 37 |
| (T) | 40 |

EXAMPLE 9

Cytotoxic Activity

The cytotoxic activity of oligonucleoside boranophosphates of the present invention was tested on the following neoplastic cell lines:

1. L1210 lymphoid leukemia cells, R. Geran et al., *Cancer Chemotherapy Reports* 3, 7 (1972).(grown in RPMI+ 15% FBS+antibiotics).
2. Tmolt$^s$ acute lymphoblastic T cell leukemia, S. Schreiber and N. Ikemoto, *Tett. Lett* 29, 3211 (1988) (grown in RPMI–1640+10% FBS).
3. Colon adenocarcinoma SW480 human colorectal carcinoma. A. Leibovitz et al., *Cancer Res.* 36, 4562 (1976) (grown in L15+10% FBS).
4. Lung bronchogenic MB-9812, S. Aronson et al., *Expt. Cell Res.* 61, 1 (1970) (grown in EMEM+10% FBS+ NEAA).
5. S. Human Osteosarcoma TE418. H. Smith et al., *Int. J. Cancer* 17, 219 (1976) (grown in DMEM +10% FBS).
6. KB epidermoid oral nesopharnyx. R. Geran, supra; H. Eagle, *Proc. Soc. Expt. Biol.* 89, 362 (1955) (grown in EMEM+5% calf serum).
7. Hela-S, ATCC-CCL 2.2, cervical carcinoma suspended, S. Schreiber and N. Ikemoto, supra; T. Puck et al., *J. Exp. Med.* 103, 273 (1956) (grown in Joklik+5% FBS, Ham's $F_{12}$+5% FBS) .
8. Breast carcinoma MDA MB157, W. Nelson Rees et al., *Int. J. Cancer* 16, 74 (1975) (grown in EMEM+10% FBS+NEAA).
9. Human glioma cell EH 118 MG transformed stain of Rous sarcoma virus, J. Lutton et al., *J. Biol. Chem.* 254, 11181 (1979) (grown in DMEM-H+10% FCS).

The cytotoxic screens were conducted according to NIH protocols, see E. Huang et al., *J. Pharm. Sci.* 61, 108 (1972), with $10^4$ cells, growth medium, antibiotics and drugs from 0.5 to 100 µg/ml final concentration. For the L1210, Hela-S, amd Tmolt, (i.e. the suspended cells), the incubations were conducted in sterile test tubes in a final volume of 1 ml for 72 hr at 37° C. in a $CO_2$ incubator. The cells on the third day were still in log growth phase. The number of cells/ml are determined using trypan blue exclusion and a hemocytometer. See, e.g., R. Geran, supra. For solid tumors $1 \times 10^4$ cells are plated with 1 ml of medium+ antibiotics and the other components of growth. When the controls have converged (≈95%) then the density of the cells is estimated and the $ED_{50}$ values calculated. These data are given in Table 3 below.

TABLE 3

Cytotoxicity of Oligodeoxynucleoside Boronophosphates

| Cpd. | L1210 | P388 | Tmolt | Adeno Carcinoma SW480 | KB | Lung Bronchogenic | Hela-S | Osteo sarcoma | Glioma |
|---|---|---|---|---|---|---|---|---|---|
| A | 3.21 | — | 2.04 | 3.53 | 3.51 | 4.60 | 3.10 | 7.28 | 4.72 |
| J |  | — | 3.16 | 0.875 |  |  | 1.88 |  | 1.77 |
| T | 3.45 | — | 3.89 | 1.48 | 0.61 | 6.53 | 2.44 |  |  |

The foregoing examples are illustrative of the present invention, and are not to be taken as restrictive thereof. The invention is defined by the following claims, with equivalents of the claims to be included therein.

That which is claimed is:

1. An oligonucleoside boranophosphate comprising a chain of up to 51 ribonucleosides or deoxyribonucleosides, or a salt thereof, containing at least one boronated internucleotide phosphodiester linkage of the formula:

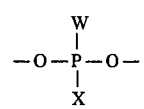

wherein:

W is selected from the group consisting of =O, =S, —OR', —SR', or —$OCH_2CH_2CN$, wherein R' is C1 to C3 alkyl;

X is selected from the group consisting of —$BH_3$, —$BH_2R_1$, —$BHR_1R_2$ and —$BR_1R_2R_3$;

$R_1$ is selected from the group consisting of —$R_4$, —COOH, —$COOR_4$, —$CONHR_4$, —CON $(R_4)_2$, —$CN^+R_4Z^-$, —CN, carboxycholesteryl and carboxybenzyl, wherein $R_4$ is C1 to C18 alkyl and $Z^-$ is an anion;

$R_2$ is selected from the group consisting of —$R_5$, —COOH, —$COOR_5$, —$CONHR_5$, —CON $(R_5)_2$, —$CN^+R_5Z^-$, —CN, carboxycholesteryl and carboxybenzyl, wherein $R_5$ is C1 to C18 alkyl and $Z^-$ is an anion; and $R_3$ is selected from the group consisting of C1 to C3 alkyl.

2. A compound of claim 1, wherein W is =O.

3. A compound of claim 1, wherein W is —$OCH_3$.

4. A compound of claim 1, wherein X is selected from the group consisting of —$BH_3$, —$BH_2R_1$, and —$BHR_1R_2$.

5. A compound of claim 1, wherein X is selected from group consisting of —BH3 and —$BH_2R_1$.

6. A compound of claim 1, wherein X is —$BH_3$.

7. A compound of claim 1, wherein $R_1$ is selected from the group consisting of —$R_4$, —COOH, —$COOR_4$, —$CONHR_4$, —CON $(R_4)_2$, —$CN^{30}$ $R_4Z^-$ and —CN, wherein $R_4$ is C1 to C6 alkyl and $Z^-$ is an anion.

8. A compound of claim 1, wherein $R_1$ is selected from the group consisting of —$R_4$, —COOH, —$COOR_4$, —$CONHR_4$, —CON $(R_4)_2$, and —CN, wherein $R_4$ is C1 to C3 alkyl.

9. A compound of claim 1, wherein $R_2$ is selected from the group consisting of —$R_5$, —COOH, —$COOR_5$, —$CONHR_5$, —CON $(R_5)_2$, —$CN^+R_5Z^-$ and —CN, wherein $R_5$ is C1 to C9 alkyl and $Z^-$ is an anion.

10. A compound of claim 1, wherein $R_2$ is selected from the group consisting of —$R_5$, —COOH, —$COOR_5$, —$CONHR_5$, —CON $(R_5)_2$, and —CN, wherein $R_5$ is C1 to C3 alkyl.

11. A compound of claim 1, wherein $R_3$ is methyl.

12. A compound of claim 1, which compound comprises a chain of deoxyribonucleosides.

13. An oligonucleoside boronophosphate, or a salt thereof, having the formula, from 5' to 3' of:

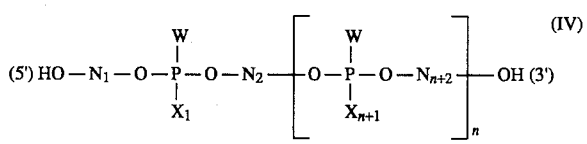

wherein:

n is an integer having a value of from 0 to 50;

W is selected from the group consisting of =O, =S, —OR', —SR', and —OCH$_2$CH$_2$CN, wherein R' is C1 to C3 alkyl;

$X_1$ and $X_{n+1}$ are each independently selected from the group consisting of —OH, —BH$_3$, —BH$_2$R$_1$, —BHR$_1$R$_2$ and —BHR$_1$R$_2$ and —BR$_1$R$_2$R$_3$, subject to the proviso that at least one of $X_1$ and $X_{n+1}$ is not —OH;

$R_1$ is selected from the group consisting of —R$_4$, —COOH, —COOR$_4$, —CONHR$_4$, —CON (R$_4$)$_2$, —CN$^+$R$_4$Z$^-$, —CN, carboxycholesteryl and carboxybenzyl, wherein R$_4$ is C1 to C18 alkyl and Z$^-$ is an anion;

$R_2$ is selected from the group consisting of —R$_5$, —COOH, —COOR$_5$, —CONHR$_5$, —CON (R$_5$)$_2$, —CN$^+$R$_5$Z$^-$, —CN, carboxycholesteryl and carboxybenzyl, wherein R$_5$ is C1 to C18 alkyl and Z$^-$ is an anion; and $R_3$ is selected from the group consisting of C1 to C3 alkyl;

$N_1$ and $N_{n+2}$ are each independently a nucleoside or deoxynucleoside monomer of the formula:

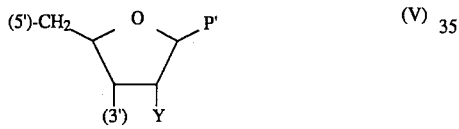

wherein Y is selected from the group consisting of —H and —OH; and wherein P' is a base of a nucleic acid selected from the group consisting of adenine, thymine, cytosine, guanine, uracil, xanthine, hypoxanthine, 5-methylcytosine, 5-bromouracil, 8-azidoadenine, and 2,6-diaminopurine.

14. A compound of claim 13, wherein P' is selected from the group consisting of adenine, thymine, cytosine, guanine, and uracil.

15. A compound of claim 13, wherein n is from 0 to 30.

16. A compound of claim 13, wherein n is from 0 to 18.

17. A compound of claim 13, wherein W is =O.

18. A compound of claim 13, wherein W is —OCH$_3$.

19. A compound of claim 13, wherein $X_1$ and $X_{n+}$ are each independently selected from the group consisting of —OH, —BH$_3$, —BH$_2$R$_1$, and —BHR$_1$R$_2$.

20. A compound of claim 13, wherein $X_1$ and $X_{n+}$ are each independently selected from the group consisting of —OH, —BH$_3$ and —BH$_2$R$_1$.

21. A compound of claim 13, wherein $X_1$ and $X_{n+1}$ are not —OH.

22. A compound of claim 13, wherein $X_1$ and $X_{n+1}$ is —BH$_3$.

23. A compound of claim 13, wherein $R_1$ is selected from the group consisting of —R$_4$, —COOH, —COOR$_4$, —CONHR$_4$, —CON (R$_4$)$_2$, —CN$^+$R$_4$Z$^-$, and —CN, wherein R$_4$ is C1 to C9 alkyl and Z$^+$ is an anion.

24. A compound of claim 13, wherein $R_1$ is selected from the group consisting of —R$_4$, —COOH, —COOR$_4$, —CONHR$_4$, —CON (R$_4$)$_2$, and —CN, wherein R$_4$ is C1 to C3 alkyl.

25. A compound of claim 13, wherein $R_2$ is selected from the group consisting of —R$_5$, —COOH, —COOR$_5$, —CONHR$_5$, —CON (R$_5$)$_2$, —CN$^+$R$_5$Z$^-$, and —CN, wherein R$_5$ is C1 to C9 alkyl and Z$^-$ is an anion.

26. A compound of claim 13, wherein $R_2$ is selected from the group consisting of —R$_5$, —COOH, —COOR$_5$, —CONHR$_5$, —CON (R$_5$)$_2$, and —CN, wherein R$_5$ is C1 to C3 alkyl.

27. A compound of claim 13, wherein $R_3$ is methyl.

28. A compound of claim 13, wherein Y is —H.

29. A pharmaceutical composition comprising a pharmaceutically acceptable carrier in combination with a therapeutically effective amount of an oligonucleoside boranophosphate comprising a chain of up to 51 ribonucleosides or deoxyribonucleosides, or a pharmaceutically acceptable salt thereof, containing at least one boronated internucleotide phosphodiester linkage of the formula:

wherein:

W is selected from the group consisting of =O, =S, —OR', and —SR' wherein R' is C1 to C3 alkyl;

X is selected from the group consisting of —BH$_3$, —BH$_2$R$_1$, —BHR$_1$R$_2$ and —BR$_1$R$_2$R$_3$;

$R_1$ is selected from the group consisting of —R$_4$, —COOH, —COOR$_4$, —CONHR$_4$, —CON (R$_4$)$_2$, —CN$^+$R$_4$Z$^-$, —CN, carboxycholesteryl and carboxybenzyl, wherein R$_4$ is C1 to C18 alkyl and Z$^-$ is an anion;

$R_2$ is selected from the group consisting of —R$_5$, —COOH, COOR$_5$, —CONHR$_5$, —CON (R$_5$)$_2$, —CN$^+$R$_5$Z$^-$, —CN, carboxycholesteryl and carboxybenzyl, wherein R$_5$ is C1 to C18 alkyl and Z$^-$ is an anion; and $R_3$ is selected from the group consisting of C1 to C3 alkyl.

30. A pharmaceutical composition of claim 29, wherein W is =O.

31. A pharmaceutical composition of claim 29, wherein W is —OCH$_3$.

32. A pharmaceutical composition of claim 29, wherein X is —BH$_3$.

33. A pharmaceutical composition of claim 29, wherein $R_1$ is selected from the group consisting of —R$_4$, —COOH, —COOR$_4$, —CONHR$_4$, —CON (R$_4$)$_2$, AND —CN, wherein R$_4$ is C1 to C3 alkyl.

34. A pharmaceutical composition of claim 29, wherein $R_2$ is selected from the group consisting of —R$_5$, —COOH, —COOR$_5$, —CONHR$_5$, —CON (R$_5$)$_2$, and —CN, wherein R$_5$ is C1 to C18 alkyl.

35. A pharmaceutical composition of claim 29, wherein $R_3$ is methyl.

36. A compound of claim 1, wherein $R_4$ and $R_5$ are each C1–C9 alkyl.

37. A pharmaceutical composition comprising a pharmaceutically acceptable carrier in combination with an effective anti-hyperlipidemic or anti-inflammatory amount of an oligonucleoside boranophosphate comprising a chain of up to 51 ribonucleosides or deoxyribonucleosides, or a pharmaceutically acceptable salt thereof, containing at least one boronated internucleotide phosphodiester linkage of the formula:

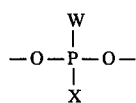
(III)

wherein:

W is selected from the group consisting of =O, =S, —OR', and —SR' wherein R' is C1 to C3 alkyl;

X is selected from the group consisting of —BH$_3$, —BH$_2$R$_1$, —BHR$_1$R$_2$ and —BR$_1$R$_2$R$_3$;

R$_1$ is selected from the group consisting of —R$_4$, —COOH, —COOR$_4$, —CONHR$_4$, —CON(R$_4$)$_2$, —CN$^+$R$_4$Z$^-$, —CN, carboxycholesteryl and carboxybenzyl, wherein R$_4$ is C1 to C18 alkyl and Z$^-$ is an anion;

R$_2$ is selected from the group consisting of —R$_5$, —COOH, —COOR$_5$, —CONHR$_5$, —CON (R$_5$)$_2$, —CN$^+$R$_5$Z$^-$, —CN, carboxycholesteryl and carboxybenzyl, wherein R$_5$ is C1 to C18 alkyl and Z$^-$ is an anion; and R$_3$ is selected from the group consisting of C1 to C3 alkyl.

38. An oligonucleoside boranophosphate comprising a chain of up to three ribonucleosides or deoxyribonucleosides, or a salt thereof, containing at least one boronated internucleotide phosphodiester linkage of the formula:

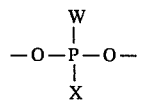
(III)

wherein:

W is selected from the group consisting of =O, =S, —OR', —SR', or —OCH$_2$CH$_2$CN, wherein R' is C1 to C3 alkyl;

X is selected from the group consisting of —BH$_3$, —BH$_2$R$_1$, —BHR$_1$R$_2$ and —BR$_1$R$_2$R$_3$;

R$_1$ is selected from the group consisting of —R$_4$, —COOH, —COOR$_4$, —CONHR$_4$, —CON (R$_4$)$_2$, —CN$^+$R$_4$Z$^-$, —CN, carboxycholesteryl and carboxybenzyl, wherein R$_4$ is C1 to C18 alkyl and Z$^-$ is an anion;

R$_2$ is selected from the group consisting of —R$_5$, —COOH, —COOR$_5$, —CONHR$_5$, —CON (R$_5$)$_2$, —CN$^+$R$_5$Z$^-$, —CN, carboxycholesteryl and carboxybenzyl, wherein R$_5$ is C1 to C18 alkyl and Z$^-$ is an anion; and R$_3$ is selected from the group consisting of C1 to C3 alkyl.

39. An oligonucleoside boranophosphate selected from the group consisting of thymidylyl[3'-5']-(3'-acetylthymidylyl) (borane) phosphonate methyl ester (or 3'-0[thymidylyl]-5'0- [3'-acetylthymidylyl ]methyl phosphite-borane; thymidylyl [3'-5']-(3'-acetylthymidylyl) (cyanoborane)phosphonate methyl ester; thymidylyl [3'-5']-(3'-acetylthymidylyl ) (carbomethoxyborane) phosphonate methyl ester; thymidylyl [3'-5'](3'-acetylthymidylyl ) (N-ethylcarbamoylborane) phosphonate methyl ester; thymidylyl[3'-5']-(3'-acetylthymidylyl) (carboxyborane) phosphonate methyl ester; thymidylyl [3'-5'] -(3'-acetylthymidylyl)(N-ethylcarbamoyl)methylborane phosphonate methyl ester; thymidylyl[3'-5']-thymidylyl(borane)-phosphonate ammonium salt; thymidylyl[3'-5']-thymidylyl(cyanoborane)-phosphonate ammonium salt; thymidylyl[3'-=]-thymidylyl(carbomethoxy)-phosphonate ammonium salt; thymidylyl[3'-5']-thymidylyl(methylborane)-phosphonate ammonium salt; thymidylyl[3'-5']-thymidylyl(N-ethyl-carbamoyl)methylborane phosphonate ammonium salt; 2'deoxycytidylyl[3'-5']-2'deoxycytidylyl-(borane)phosphonate ammonium salt; 2'deoxycytidylyl[3'-5']-2'deoxycytidylyl-(cyanoborane)phosphonate ammonium salt; thymidylyl [3'-5']thymidylyl[3'-5'](3'-acetylthymidylyl) boranephosphonate dimethyl ester; and thymidylyl[3'-5'] thymidylylboranephosphonate[3'-540 ](3'-acetylthymidylyl) cyanoboranephosphonate dimethyl ester.

* * * * *

UNITED STATES PATENT AND TRADEMARK OFFICE
CERTIFICATE OF CORRECTION

PATENT NO. : 5,455,233

DATED : October 3, 1995

INVENTOR(S) : Spielvogel et al.

It is certified that error appears in the above-identified patent and that said Letters Patent is hereby corrected as shown below:

Column 1, line 24, please correct " Ts'so " to read -- Ts'o --.

Column 3, line 8, please correct " (III) " to read -- (II) --.

Column 3, lines 36, 38, 39, 52 and 53, please correct " 2'O" to read -- 2'-O -- .

Column 4, line 7, please correct " 3'O " to read -- 3' -O--

Column 6, line 63, please correct " Y-P " to read -- Y-P-Q -- .

Column 16, line 34, please correct " $-CN^{30} R_4Z^-$ " to read -- $-CN^+R_4Z^-$ --.

Column 16, line 35, please correct " C6 " to read -- C9 --.

UNITED STATES PATENT AND TRADEMARK OFFICE
CERTIFICATE OF CORRECTION

PATENT NO. : 5,455,233
DATED : October 3, 1995
INVENTOR(S) : Spielvogel et al.

It is certified that error appears in the above-identified patent and that said Letters Patent is hereby corrected as shown below:

Column 17, Claim 19, line 54, please correct " $X_{n+}$ " to read -- $X_{n+1}$ --.

Column 17, Claim 20, line 57, please correct " $X_{n+}$ " to read -- $X_{n+1}$ --.

Column 17, Claim 23, line 67, please correct " $Z^+$ " to read -- $Z^-$ --.

Column 18, Claim 29, line 39, please correct "$COOR_5$" to read -- $-COOR_5$ --.

Column 20, Claim 39, line 27, please correct "[3'-=]" to read -- [3'-5'] --.

Column 20, Claim 39, line 37, please correct "[3'-540]" to read -- [3'-5'] --.

Signed and Sealed this

Seventeenth Day of September, 1996

Attest:

BRUCE LEHMAN

*Attesting Officer*     *Commissioner of Patents and Trademarks*